US012629400B2

(12) United States Patent
Ohemeng et al.

(10) Patent No.: US 12,629,400 B2
(45) Date of Patent: May 19, 2026

(54) PHARMACEUTICAL COMPOSITIONS AND METHODS FOR TREATING OR PREVENTING BACTERIAL INFECTIONS IN HUMANS AND IN ANIMALS

(71) Applicant: LaGray, Inc., Chicago, IL (US)

(72) Inventors: Kwasi Adomako Ohemeng, Tema (GH); Peace Mawunyo Doe, Mataheko-Afienya (GH); Samuel Nda Blay Armah, Dansoman (GH); Kwabena Oteng-Boahen, Accra (GH); Vanessa Naomi Opare, Pokuase (GH); Paul Asong Lartey, Chicago, IL (US)

(73) Assignees: LaGray, Inc.; Equatorial Healthcare Services (GH)

( * ) Notice: Subject to any disclaimer, the term of this patent is extended or adjusted under 35 U.S.C. 154(b) by 233 days.

(21) Appl. No.: 18/754,975

(22) Filed: Jun. 26, 2024

(65) Prior Publication Data

US 2025/0000925 A1      Jan. 2, 2025

Related U.S. Application Data

(60) Provisional application No. 63/523,811, filed on Jun. 28, 2023.

(51) Int. Cl.
| | |
|---|---|
| *A61K 36/00* | (2006.01) |
| *A61K 36/19* | (2006.01) |
| *A61P 31/04* | (2006.01) |

(52) U.S. Cl.
CPC ............. *A61K 36/19* (2013.01); *A61P 31/04* (2018.01); *A61K 2236/15* (2013.01); *A61K 2236/17* (2013.01); *A61K 2236/33* (2013.01); *A61K 2236/39* (2013.01)

(58) Field of Classification Search
CPC .................................................... A61K 36/19
See application file for complete search history.

(56) References Cited

U.S. PATENT DOCUMENTS

| | | | |
|---|---|---|---|
| 10,688,143 B2 | 6/2020 | Yoon et al. | |
| 10,869,904 B2 | 12/2020 | Yoon et al. | |
| 11,534,471 B2 | 12/2022 | Ngwa | |
| 11,712,056 B2 | 8/2023 | Peltier et al. | |
| 2004/0062823 A1 | 4/2004 | Obukowicz et al. | |
| 2017/0360862 A1 | 12/2017 | Yoon et al. | |
| 2023/0143345 A1 | 5/2023 | Yoon et al. | |

OTHER PUBLICATIONS

Umoh et al., Pharmacognostic evaluation of the leaves and stems of Justicia secunda Vahl. (acanthaceae). World Journal of Pharmaceutical Research (2020), 9(11Spec.Iss.), 5-18 (Year: 2020).*

Written Opinion of the International Searching Authority, dated Aug. 22, 2025, corresponding to related International Application No. PCT/US2025/032869.

Bako, "Lupeol and lauric acid isolated from ethyl acetate stem extract of Justicia secunda and their antimicrobial activity" 081-094, J. Chem. Soc. Nigeria. Online, 2023, abstract; p. 82, col. 1, para 1 and col. 2, para 1; p. 83, col. 1, para 2 and col. 2, para 1; p. 92, col. 2, para 2.

Soos, "Mineral content of propolis tinctures in relation to the extraction time and the ethanol content of the extraction solvent" 719-726, LWT—Food Science and Technology. Online, May 21, 2019; <DOI: https://doi.org/10.1016/j.lwt.2019.05.090>, p. 725, col. 1, paragraph 2, and col. 2, paragraph I.

Łukasz Świątek, "Chemical Characterization of Different Extracts of Justicia secunda Vahl and Determination of Their Anti-Oxidant, Anti-Enzymatic, Anti-Viral, and Cytotoxic Properties", DOI Foundation, Feb. 17, 2023, available at: https://www.mdpi.com/2076-3921/12/2/509 (last accessed Jun. 26, 2024).

* cited by examiner

*Primary Examiner* — Qiuwen Mi
(74) *Attorney, Agent, or Firm* — Kaspar Law Company, LLC; Scott R. Kaspar

(57) ABSTRACT

A pharmaceutical composition having antibiotic qualities is disclosed. The pharmaceutical composition includes a plurality of leaves and stems of the plant *Justicia secunda*, wherein the plurality of leaves and stems dried and pulverized to form a coarse powder; and an organic solvent, the coarse powder combined with the organic solvent for one to ten days, but preferably seven days, to form an organic solvent extract that yields a powder composition under column chromatography.

15 Claims, 4 Drawing Sheets

PHARMACEUTICAL COMPOSITIONS AND METHODS FOR TREATING OR PREVENTING BACTERIAL INFECTIONS IN HUMANS AND IN ANIMALS

CROSS-REFERENCE TO RELATED APPLICATION

This claims the benefit of priority to U.S. Provisional Patent Application No. 63/523,811 filed Jun. 28, 2023, which is incorporated by reference herein in its entirety.

TECHNICAL FIELD

The present invention relates to pharmaceutical compositions and methods for treating or preventing bacterial infections in humans and in animals. More specifically, the present invention relates to preparation and uses of extracts and compositions of the plant *Justicia secunda*.

BACKGROUND

Antimicrobial resistance is currently a major problem in the treatment of infectious diseases, as bacterial species are becoming increasingly resistant to existing antibacterial drugs. Bacterial species such as methicillin resistant *Staphylococcus aureus* (MRSA), vancomycin resistant Enterococci (VRE) and drug resistant *Streptococcus pneumoniae* (DRSP) are resistant to several major classes of antibacterial drugs. Examples of such antibacterial drugs are the quinolone ciprofloxacin, the tetracycline minocycline and the glycopeptide vancomycin. There is therefore an urgent need for novel antibacterial drugs, especially pharmaceutical compositions that are effective in treating infections by resistant strains of bacteria including MRSA, VRE and DRSP.

As recognized by those skilled in the art, most antibacterial drugs in current use are compositions of microbial fermentation extracts, semi-synthetic derivatives of such compositions or compounds obtained through organic synthesis. For example, ciprofloxacin is a purely synthetic compound, minocycline is a semi-synthetic derivative of a composition from the fermentation of a strain of *Streptomyces aurofaciens*, and vancomycin is a composition from the fermentation of a strain of *Amycolatopsis orientalis*.

This invention relates to the use of extracts, fractions, or compositions of a plant which to our surprise, have potent activity against bacteria. More particularly, the invention relates to pharmaceutical compositions derived from an organic solvent extract of the plant *Justicia secunda* and their use in the treatment or prevention of bacterial infections. These compositions are potent against bacterial strains that are either susceptible or resistant to the antibacterial drugs ciprofloxacin, minocycline and vancomycin.

SUMMARY OF THE INVENTION

According to one non-limiting aspect of the present disclosure, an example embodiment of a pharmaceutical composition having antibiotic qualities is disclosed. The pharmaceutical composition includes a plurality of leaves and stems of the plant *Justicia secunda*, wherein the plurality of leaves and stems dried and pulverized to form a coarse powder; and an organic solvent, the coarse powder combined with the organic solvent for one to ten days, but preferably seven days, to form an organic solvent extract that yields a powder composition under column chromatography.

According to another non-limiting aspect of the present disclosure, an example embodiment of method of preparing a pharmaceutical composition is disclosed. The method includes: providing a plurality of leaves and stems of the plant *Justicia secunda*; drying the plurality of leaves and stems; pulverizing the plurality of leaves and stems to form a coarse powder; providing an organic solvent; combining the coarse powder with the organic solvent for one to ten days, but preferably seven days; filtering the organic solvent to provide an organic solvent extract; and separating the organic solvent extract using column chromatography to yield a powder composition.

Additional features and advantages are described herein, and will be apparent from the following Detailed Description and the figures.

BRIEF DESCRIPTION OF THE DRAWINGS

Features and advantages of the system and method described herein may be better understood by reference to the accompanying drawings in which.

A skilled artisan will appreciate the foregoing details, as well as others, upon considering the following Detailed Description of certain non-limiting embodiments of the pharmaceutical composition according to the present disclosure. One of ordinary skill also may comprehend certain of such additional details upon using system and method described herein.

DETAILED DESCRIPTION

The present invention comprises preparation and use of novel antibacterial compositions from the plant *Justicia secunda*. These novel compositions exert a broad spectrum of antibacterial activity towards several bacterial species and strains. In particular, the pharmaceutical compositions of this invention exert potent antibacterial activity against pathogenic bacterial strains that are resistant to conventional antibacterial drugs, including ciprofloxacin, minocycline, and vancomycin. Specifically, compositions from this invention are effective against MRSA, VRE and DRSP. A method of preparation of the pharmaceutical compositions and methods of treating bacterial infections are described.

Figure 1:
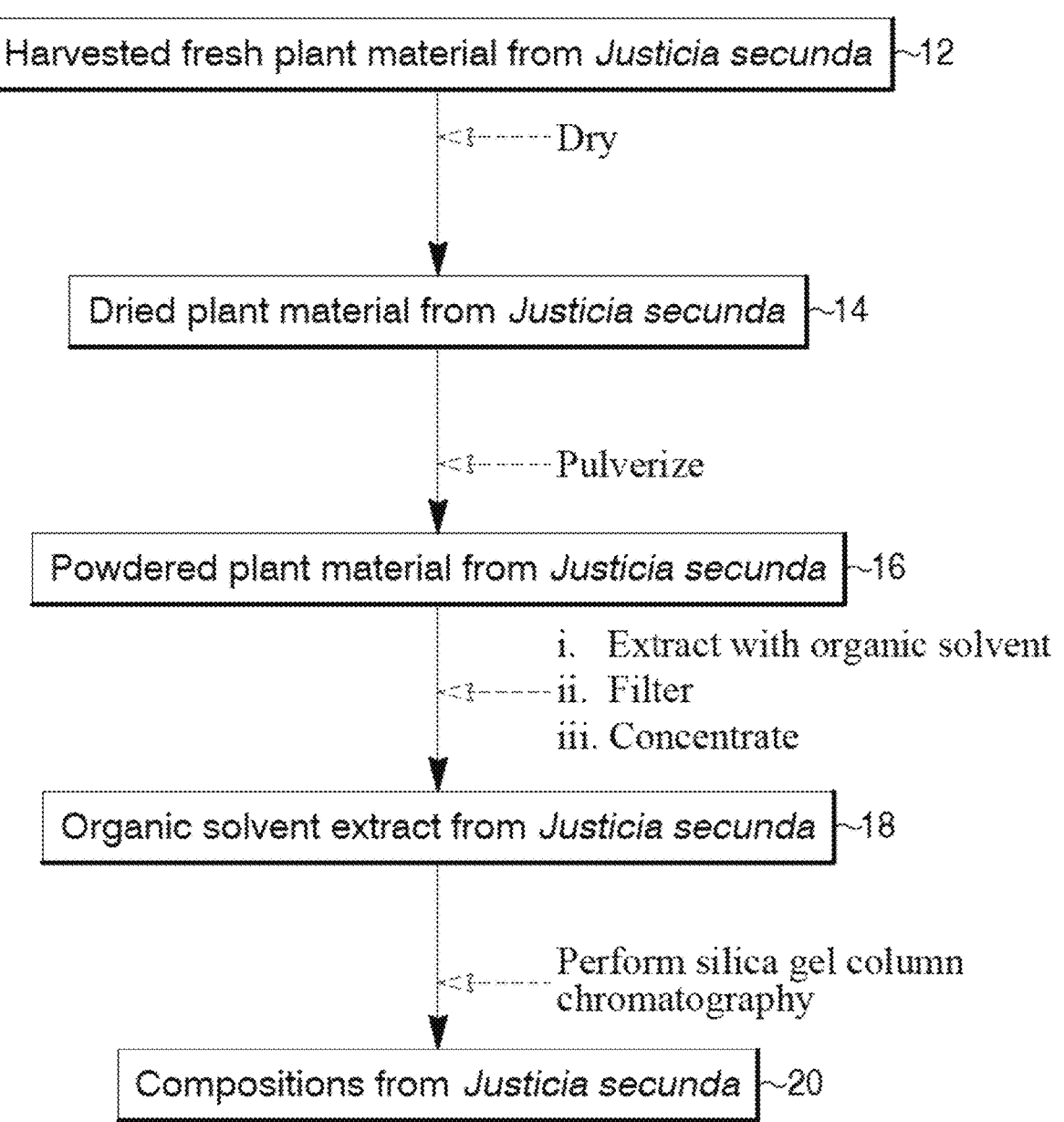
FIG. 1 is a schematic diagram of the preferred method of preparation of a pharmaceutical composition from the plant *Justicia secunda*, involving the preparation of an organic solvent extract of the plant and preparation of compositions of the plant from the organic solvent extract.

As shown in FIG. 1, a schematic diagram of the preferred method of preparation of a pharmaceutical composition from the plant *Justicia secunda* is disclosed. The preferred method relates to the preparation of an organic solvent extract of the plant and preparation of compositions of the plant from the organic solvent extract.

In a preferred embodiment and referring to FIG. 1, parts of the plant *Justicia secunda* that include leaves, stems, branches, and roots, but more preferably leaves and stems, referred to as plant material are selected for use, as shown at reference numeral 12.

The plant material is dried in the sun or in an oven to a suitable dryness or moisture content, as shown at reference numeral 14.

The plant material is pulverized to provide a fine to a coarse powder, but more preferably a coarse powder, as shown at reference numeral 16.

The powder is soaked for one to ten days, but more preferably 7 days in an organic solvent such as methyl alcohol, ethyl alcohol, propyl alcohol, butyl alcohol or isopropyl alcohol, but more preferably methyl alcohol, as shown at reference numeral 18. The mixture is filtered and subjected to vacuum evaporation to provide the organic solvent extract.

The organic solvent extract is subjected to column chromatography using silica gel as the stationary phase and 10 to 30% ethyl acetate in hexane as the mobile phase, but more preferably 20% ethyl acetate in hexane, as shown at reference numeral 20.

Fractions containing compositions in the organic solvent extract are collected and analyzed by thin layer chromatography, in this particular case, using silica gel as the stationary mately 0.49. The illustration of FIG. 3 likewise shows Example 1 to be a pure chemical entity with an HPLC retention time of about 26.6 minutes on a C18 column.

Figure 3:
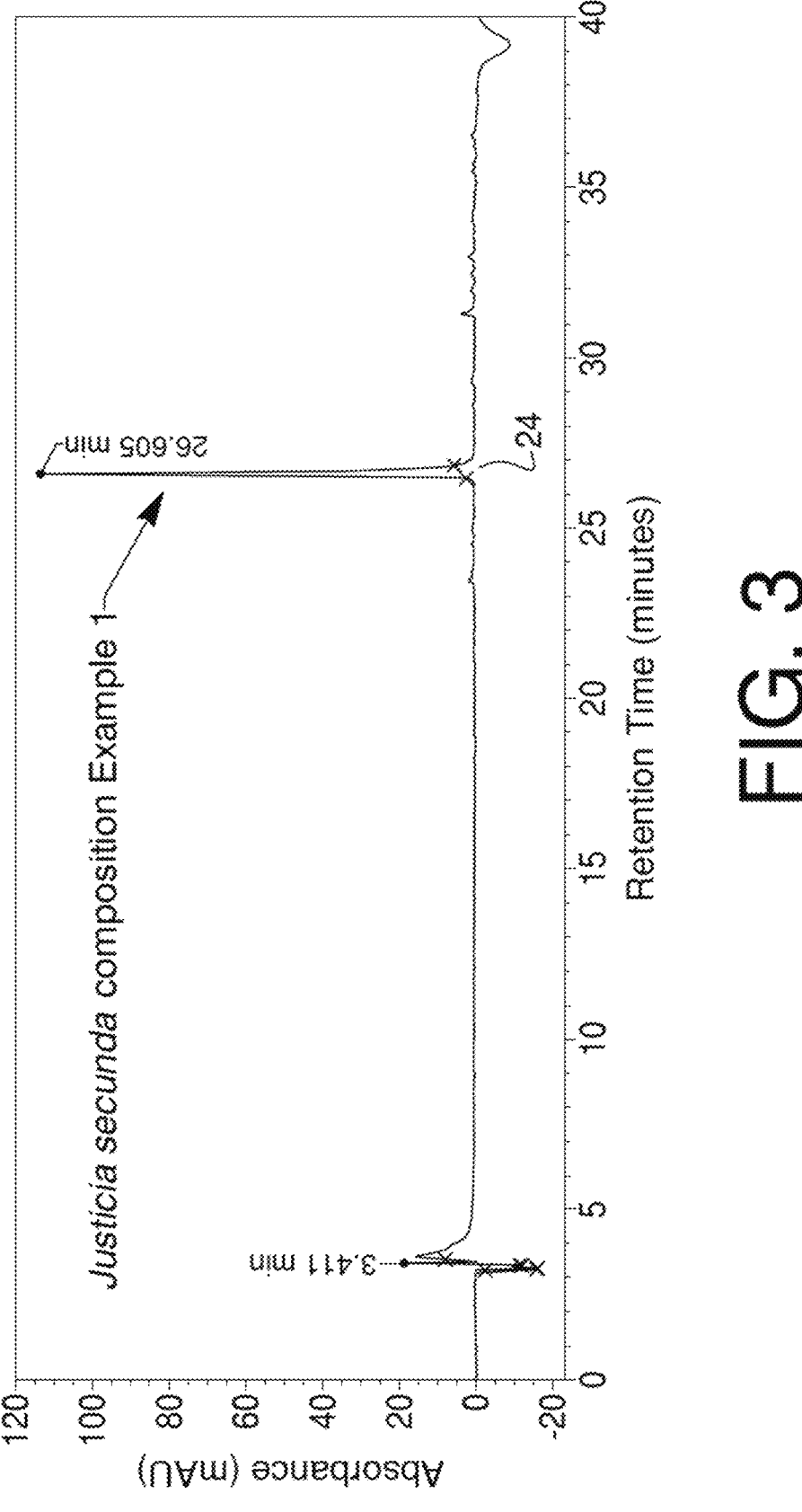
FIG. 3 shows the position in a tracing from a High-Performance Liquid Chromatography ("HPLC") analysis of a pharmaceutical composition prepared from the organic solvent extract of *Justicia secunda* relating to Example 1.

FIG. 3 shows the position in a tracing from a High-Performance Liquid Chromatography ("HPLC") analysis of a pharmaceutical composition prepared from the organic solvent extract of *Justicia secunda*. In this particular case, the HPLC results are for Example 1, as shown at reference numeral 24. This figure is presented as an illustration only, as the antibacterial properties of a second composition Example 2, derived likewise from the organic extract of *Justicia secunda* shall be described together with the antibacterial properties of Example 1.

Figure 4:
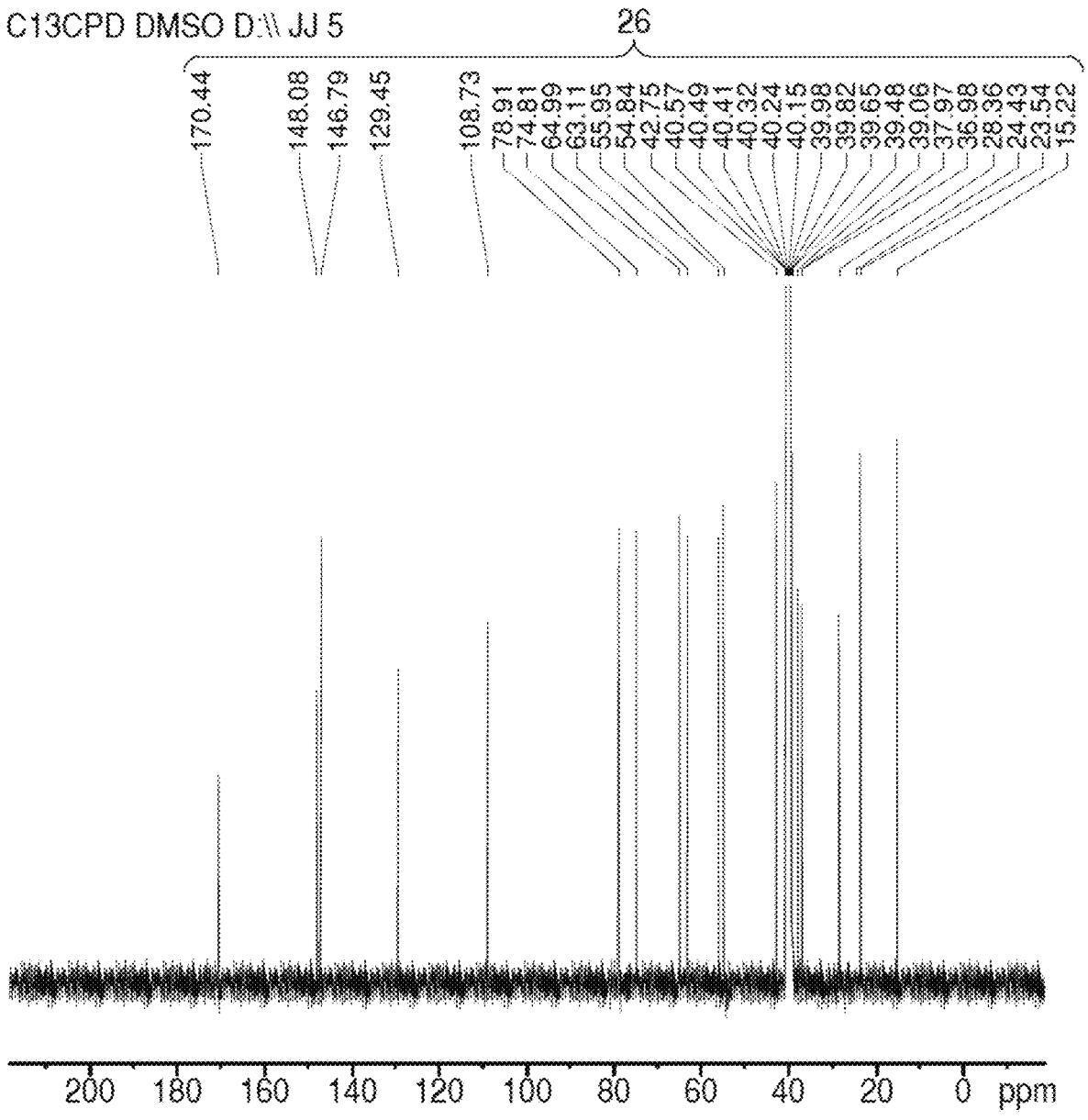
FIG. 4 shows the $^{13}$C nuclear magnetic resonance spectrum of Example 1.

FIG. 4 shows the $^{13}$C nuclear magnetic resonance spectrum of Example 1. As shown at reference numeral 26, FIG. 4 shows certain details of the $^{13}$C nuclear magnetic resonances that are characteristic of Example 1, and together with other structural data depict the molecular structure of Example 1.

Antibacterial Activity

Example 1 and Example 2 were evaluated for antibacterial activity using the agar dilution method to determine the degree of in vitro susceptibility of aerobic bacteria to the compositions from *Justicia secunda*. The results for the compositions are shown in TABLE I together with the results obtained for ciprofloxacin, minocycline and vancomycin, which are antibacterial drugs in current clinical use, and used herein as positive controls.

TABLE 1

| | MIC (µg/mL) | | | | |
| --- | --- | --- | --- | --- | --- |
| Bacterial Species (Strain) | Example 1 | Example 2 | Positive Control Ciprofloxacin | Positive Control Minocycline | Positive Control Vancomycin |
| *Staphylococcus aureus* | 0.12 | 0.5 | 0.06 | 0.25 | 0.13 |
| *S. aureus* (MRSA) | 0.25 | 1.00 | 32.0 | 8.00 | 2.00 |
| *Enterococcus faecium* | 0.12 | 0.12 | 0.50 | 0.50 | 1.00 |
| *E. faecium* (VRE) | 1.00 | 0.5 | 2.00 | 16.0 | 125 |
| *Streptococcus pneumoniae* | 0.25 | 0.5 | 0.13 | 0.50 | 0.25 |
| *S. pneumoniae* (DRSP) | 0.12 | 1.00 | 2.00 | 16.0 | 0.50 |
| *Streptococcus pyogenes* | 1.00 | 0.30 | 0.50 | 0.12 | 0.06 |
| *Clostridium difficile* | 0.50 | 1.0 | 0.13 | 0.50 | 0.50 |
| *Hemophilus influenzae* | 0.06 | 0.25 | 0.15 | 0.25 | 0.06 |
| *Moraxella catarrhalis* | 0.25 | 0.12 | 0.25 | 0.03 | 0.01 |
| *Klebsiella pneumoniae* | 0.13 | 0.50 | 0.06 | 0.13 | 0.50 |
| *Chlamydia pneumoniae* | 0.25 | 0.25 | 0.12 | 0.50 | 0.50 |
| *Legionella pneumophila* | 0.06 | 0.12 | 0.06 | 0.12 | 0.06 | phase and 20% ethyl acetate in hexane as the mobile phase, as shown at reference numeral 20 in FIG. 1. Fractions containing identical compositions are pooled together. The pooled fractions are evaporated to yield the compositions as powders.

Figure 2:
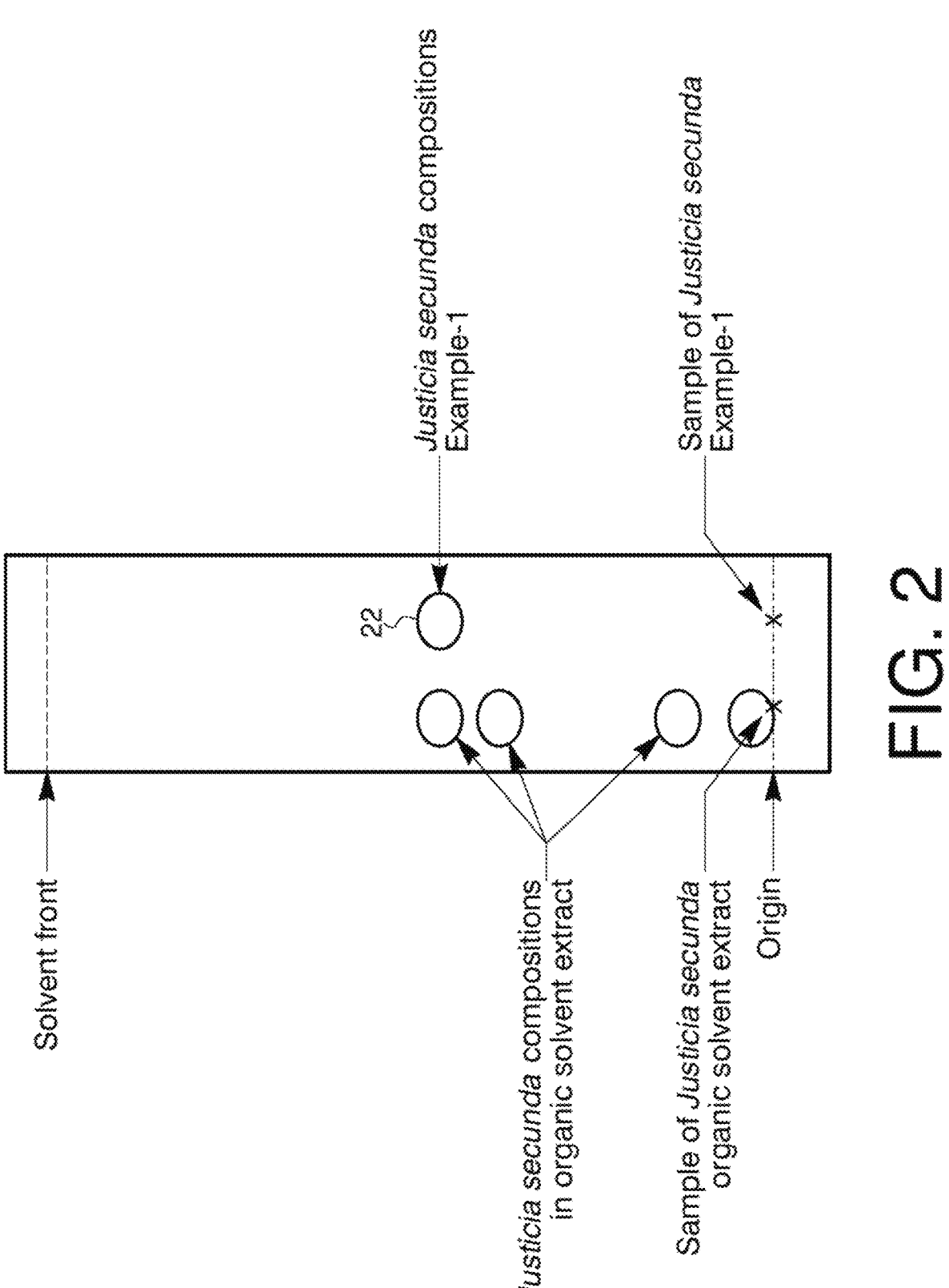
FIG. 2 is an illustrative representation of a thin layer chromatogram showing compositions in an organic solvent extract of the plant *Justicia secunda* and a discrete composition described herein and hereafter referred to as "Example 1"

FIG. 2 is an illustrative representation of a thin layer chromatogram showing compositions in an organic solvent extract of the plant *Justicia secunda*. FIG. 2 also illustrates that there are at a minimum four (4) compositions of the plant in the organic solvent extract, and further shows a discrete composition dubbed Example 1, as shown at reference numeral 22 in FIG. 2. Example 1 is prepared by the method shown in FIG. 1.

The compositions are analyzed for purity, in accordance with the steps shown in FIG. 2, for the TLC analysis of Example 1 and in FIG. 3 for the HPLC analysis of Example 1. The illustration of FIG. 2 shows Example 1 to be a pure chemical entity with a TLC retardation factor of approxi- As illustrated by TABLE 1, Example 1 and Example 2 are either equivalent or superior in activity to the positive controls against susceptible bacteria. Additionally, Example 1 and Example 2 are active against resistant strains such as MRSA, VRE and DRSP against which in several instances, the positive controls were ineffective.

Pharmaceutical Composition

The present invention includes one or more of the compositions of *Justicia secunda*, including Example 1, and pharmaceutically acceptable salts thereof, formulated together with one or more non-toxic pharmaceutically acceptable compositions such as carriers, diluents, adjuvants, binders, vehicles and the like, collectively referred to as excipients, into pharmaceutical dosage forms. In these forms, the compositions can be administered to humans and animals either orally, rectally, parenterally, intracisternally, intravaginally, intraperitoneally, intraurethrally or locally.

While the present invention has been described in terms of particular embodiments and applications, in both summarized and detailed forms, it is not intended that these descriptions in any way limit its scope to any such embodiments and applications, and it will be understood that many substitutions, changes and variations in the described embodiments, applications and details of the method illustrated herein can be made by those skilled in the art without departing from the spirit and scope of this invention.

It is therefore intended that such changes and modifications be covered by the appended set of claims.

What is claimed is:

1. A pharmaceutical composition comprising:
   a plurality of leaves and stems of the plant *Justicia secunda*, the plurality of leaves and stems dried and pulverized to form a coarse powder; and
   an organic solvent, the coarse powder combined with the organic solvent for at least one day to form an organic solvent extract that yields a powder composition under column chromatography.

2. The pharmaceutical composition of claim 1 wherein the organic solvent is selected from the group consisting of methyl alcohol, ethyl alcohol, propyl alcohol, butyl alcohol, and isopropyl alcohol.

3. The pharmaceutical composition of claim 1 wherein the organic solvent is methyl alcohol.

4. The pharmaceutical composition of claim 1 wherein the coarse powder is combined with the organic solvent for more than one day but less than ten days.

5. The pharmaceutical composition of claim 1 wherein the coarse powder is combined with the organic solvent for seven days.

6. The pharmaceutical composition of claim 1 wherein the powder composition has antibacterial qualities.

7. The pharmaceutical composition of claim 1 wherein the powder composition has antibiotic qualities.

8. A method of preparing a pharmaceutical composition, the method comprising the steps of:
   providing a plurality of leaves and stems of the plant *Justicia secunda;*
   drying the plurality of leaves and stems;
   pulverizing the plurality of leaves and stems to form a coarse powder;
   providing an organic solvent;

combining the coarse powder with the organic solvent for at least one day;
   filtering the organic solvent to provide an organic solvent extract; and
   separating the organic solvent extract using column chromatography to yield a powder composition.

9. The method of claim 8 wherein the organic solvent is selected from the group consisting of methyl alcohol, ethyl alcohol, propyl alcohol, butyl alcohol, and isopropyl alcohol.

10. The method of claim 8 wherein the organic solvent is methyl alcohol.

11. The method of claim 8 wherein the coarse powder is combined with the organic solvent for more than one day but less than ten days.

12. The method of claim 8 wherein the coarse powder is combined with the organic solvent for seven days.

13. The method of claim 8 wherein silica gel is used as the stationary phase and between 10% and 30% ethyl acetate in hexane as the mobile phase in the column chromatography.

14. The method of claim 8 wherein silica gel is used as the stationary phase and 20% ethyl acetate in hexane as the mobile phase in the column chromatography.

15. A method of preparing an antibiotic powder, the method comprising the steps of:
   providing a plurality of leaves and stems of the plant *Justicia secunda;*
   drying the plurality of leaves and stems;
   pulverizing the plurality of leaves and stems to form a coarse powder;
   providing a methyl alcohol solution;
   combining the coarse powder with the methyl alcohol solution for at least one day;
   filtering the methyl alcohol solution to provide an organic solvent extract; and
   separating the organic solvent extract using column chromatography to yield an antibiotic powder composition, the column chromatography using silica gel as the stationary phase and 20% ethyl acetate in hexane as the mobile phase.

* * * * *